United States Patent [19]

Ishimaru

[11] 4,022,773
[45] May 10, 1977

[54] CEPHALOSPORIN ESTERS

[76] Inventor: Toshiyasu Ishimaru, D-14, 2-7, Momoyamadai, Suita, Japan

[22] Filed: Aug. 25, 1975

[21] Appl. No.: 607,363

[30] Foreign Application Priority Data

Aug. 29, 1974 Japan .............................. 49-99581
Apr. 14, 1975 Japan .............................. 50-45447

[52] U.S. Cl. .......................... 260/243 C; 424/246; 260/239.1
[51] Int. Cl.² ...................................... C07D 501/20
[58] Field of Search .............................. 260/243 C

[56] References Cited

UNITED STATES PATENTS 3,852,281  12/1974  Verweij ........................... 260/243 C
3,856,785  12/1974  Breuer ............................ 260/243 C
3,879,398  4/1975   Ellerton et al. ................. 260/243 C Primary Examiner—Nicholas S. Rizzo
Attorney, Agent, or Firm—Hubbell, Cohen, Stiefel & Gross

[57] ABSTRACT

New esters of 7-acylamino-3-substituted-3-cephem-4-carboxylic acids and 1-oxides thereof have been prepared. The compounds are of value as intermediates for the preparation of various important cephalosporins.

9 Claims, No Drawings

CEPHALOSPORIN ESTERS

The present invention relates to cephalosporin esters and 1-oxides thereof and a process for the preparation of the same.

More particularly, the present invention provides new esters of 7-acylamino-3-substituted-3-cephem-4-carboxylic acids and 1-oxides thereof which can be represented by the general formula:

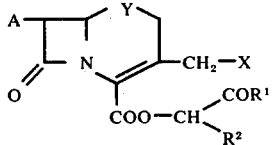

wherein A is an acylamino group; Y is =S or =S—O ; X is a hydrogen atom or a lower alkanoyloxy group; $R^1$ is a lower alkoxy, lower aralkyl or aryl group and $R^2$ is a hydrogen atom or a lower alkyl, lower alkoxycarabonyl, lower alkylcarbonyl, aralkylcarbonyl or arylcarbonyl group. or a group of the formula :

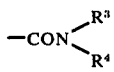

in which $R^3$ and $R^4$ which may be the same or different, are hydrogen atoms, aryl groups or lower alkyl groups which may form a heterocyclic ring together with an oxygen or nitrogen atom, and also a process for the preparation of the same.

7-Acylamino-cephem-4-carboxylic acids have been heretofore prepared by heating penicillin ester 1-oxides in the presence of a catalyst and de-esterifying the resulting 7-acylamino-cephem-4-carboxylic acid esters. However, the ester groups used herein have been limited to ones which can be easily de-esterified especially under an acidic condition, because, when ester groups of the resulting 7-acylamino-cephem-4-carboxylic acid esters are removed, the double bond in the cephem ring tends easily to migrate. The esters which have been industrially employed, were the trialkylsilyl ester, 2,2,2-trichloroethyl ester and p-nitrobenzyl ester.

It is an object of the invntion to provide new esters of 7-acylamino-3-substituted-3-cephem-4-carboxylic acids, the ester parts of which can be easily removed under a weak alkaline or acidic condition, without accompanying any migration of the double bond in the cephem ring.

Another object of the invention is to provide indusrially valuable esters of 7-acylamino-3-substituted-3-cephem-4-carboxylic acids which are intermediates for various important cephalosporins. Further objects and features of the invention will become apparent in the following description.

In the general formula (I) as mentioned above, preferred examples of the symbol A include phenylacetamido, phenoxyacetamido, formylamino, phthalimido, 2,2-dimethyl-3-nitroso-4-phenyl-5-oxoimidozolin-1-yl or 2-methyl-3-nitroso-4-phenyl-5-oxoimidazolin-1-yl group and the like. The more preferred examples are phenylacetamido and phenoxyacetamido groups. The most preferred example of the symbol X is hydrogen atom. As suitable examples of

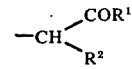

may be mentioned diacetylmethyl, acetyl-benzoylmethyl, dibensoylmethyl, acetylmethoxycarbonylmethyl, acetyl-ethoxycaronylmethyl, benzoylethoxycarbonylmethyl, di(methoxylcarbonyl)methyl, di(ethoxycarbonyl)methyl, acetyl-N,N-dimethylaminocarbonylmethyl, acetyl-morpholino-4-yl-carbonylmethyl or acetyl-aminocarbonylmethyl and the like. The preferred examples are acetylmethoxycarbonylmethyl (i.e., 1-methoxycarbonyl-2-oxopropan-1-yl) group or diacetymethyl (i.e., 2,4-dioxopentan-3-yl) group.

As specific examples of the compounds (I) according to the invention may be mentioned : 2′,4′-dioxopentan-3′-yl ester of 7-phenylacetamido-3-methyl-3-cephem-4-carboxylic acid and its 1-oxide, 1′-methoxycarbonyl-2′-oxopropan-1′-yl ester of 7-phenylacetamido-3-methyl-3-cephem-4-carboxylic acid and its 1-oxide, acetyl-benzoylmethyl ester of 7-phenylacetamido-3-methyl-3-methyl-3-cephem-4-carboxylic acid and its 1-oxide, 1′-ethoxycarbonyl-2-′-oxopropan:1′-yl ester of 7-phenylacetamido-3-methyl-3-cephem-4-carboxylic acid and its 1-oxide, benzoyl -ethoxycarbonylmethyl ester of 7-phenylacetamido-3-methyl-3-cephem-4-carboxylic acid and its 1-oxide, acetyl-N,N-dimethylaminocarabonylmethyl eser of 7-phenylacetamido-3-methyl-3-cephem-4-carboxylic acid and its 1-oxide, acetyl-morpholino-4′-yl-carbonylmethyl ester of 7-phenylacetamido-3-methyl-3-cephem-4-carboxylic acid and its 1-oxide, and the corresponding 7-phenoxyacetamido compounds.

An interesting class of the compounds (I) includes 1′-methoxycarbonyl-2′-oxopropan-1′-yl ester of 7-phenyl (or phenoxy)-acetamido-3-methyl-3-cephem-4-carboxylic acid, 1′-ethoxycarbonyl-2′-oxopropan-1′-yl-ester of 7-phenyl(or phenoxy)acetamido-3-methyl-3-cephem-4-carboxylic acid, 2′,4′-dioxopentan-3′-yl ester of 7-phenyl(or phenoxy)-acetamido-3-methyl-3-cephem-4-carboxylic acid and 1-oxides thereof.

The compounds (I) of X being hydrogen atom may be prepared, e. g., by heating a penicillin ester 1-oxide having the general formula:

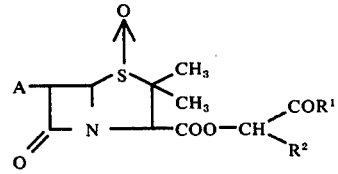

,wherein A, $R^1$ and $R^2$ are the same as defined in the formula (I), in an inert solvent and in the presence of a catalyst, and further, if needed, oxidizing the resulting 7-acylamino-3-methyl-3-cephem-4-carboxylate.

Also, the above penicillin ester 1-oxide may be prepared by reacting an appropriate penicillin such as penicillin G or V with a halogeno compound of the formula:

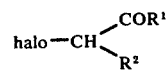

in which "halo" is a halogen atom such as chlorine or bromine atom and $R^1$ and $R^2$ are the same as defined above, and then oxidizing the resulting ester with an oxidizing agent such as peracetic acid, perbenzoic acid or hydrogen peroxide.

As the catalysts used may be mentioned pyridine dichloromethylphosphonate, picoline trichloromethylphosphonate pyridine phosphate, pyridine 2,2,2-trichloroethylphosphate; piperidine hydrogen bromide and a little amount of an acid; toluenesulfonic acid and pyridine; pyridine hydrogen bromide and pyridine; salton and pyridine; phenylphosphoric acid and pyridine; phosphorus oxybromide and pyridine; or phosphorus tribromide and pyridine.

As examples of the inert solvents may be mentioned dioxane, toluene, trichloroethane, dimethylformamide, dimethylacetamide, dimethylsulfoxide or the like.

When the compounds (I) of X being lower alkanoyloxy group are desired, they may be prepared by bromination of the methyl group of the compounds (I) in which X is hydrogen atom and Y is preferably =S—0, with N-bromosuccinimide or N-bromoacetamide and the subsequent reaction of the resulting 3-bromomethyl compound with a salt of lower alkanoic acids.

The ester groups of the compounds (I) according to the invention, can be easily removed by hydrolysis with e.g., with an base, nitrous acid or its salt or ester, or nitrosyl halide.

The following examples are given for the purpose of illustrating the present invention.

EXAMPLE 1

A mixture of 4.5 g of 2',4'-dioxopentan-3'-yl ester of 6-phenylacetamido-penam-3-carboxylic acid 1-oxide, mp. 55°–60° C and 84 mg of pyridine salt of 2,2,2-trichloroethylophosphoric acid in 30 ml of anhydrous dioxane was heated at 98°–101° C while stirring. After completing the reaction, the reaction mixture was cooled to room temperature and the solvent was removed in vacuo. Methylene chloride and water were added to the residue, which then was adjusted to pH 7.5. The organic layer was washed with an aqueous sodium chloride solution, dried and distilled in vacuo. The resulted residue was purified by a silica-gel chromotagraphy (benzene : ethyl acetate) to yield 3.5 g (82%) of 2', 4'-dioxopentan-3'-yl ester of 7-phenlyacetamido-3-methyl-3-cephem-4-caroxylic acid. mp 186°–188° C (decomp.) from ethyl acetate and ethyl ether.

IR : 1765 cm$^{-1}$ ($\beta$-lactam), UV $\lambda$max : 260 n.m.
Elemental Analysis for $C_{21}H_{22}N_2O_6S$,
Calculated; C 58.39 ,H 5.15, N 6.20.
Found; C 58.21 ,H 5.19, N 6.17.

The resultant was oxidized with 40% peracetic acid in methylene chloride. The reaction was monitored by TLC. After completing the reaction, the mixture was diluted with ice-water and adjusted to pH 7.3 with ammonia. The organic layer separated was washed with an aqueous sodium chloride solution, dried and evaporated in vacuo. The residue was treated with isopropanol and petroleum ether to obtain 2', 4'-dioxopenton-3'-yl ester of 7-phenylacetamido-3-methyl-3-cephem-4-carboxylic acid 1-oxide (yield : 95%). mp. 115°–143° C (decomp.) , IR : 1775 cm$^{-1}$, UV $\lambda$max : 254 n.m.

EXAMPLE 2

A mixture of 4.15 g of 1'-methoxycarbonyl-2'-oxopropan-1'-yl ester of 6-phenylacetamido-penam-3-carboxylic acid 1-oxide, 73 mg of pyridine salt of dichloromethylphosphonic acid in 30 ml of anhydrous dioxane was heated 98°–101° C, while stirring. After 4–7 hours, the reaction mixture was cooled and evaporated in vacuo to remove the solvent. Methylene chloride and water were added to the residue, and the mixture was adjusted to pH 7.0–7.5. The aqueous layer was extracted several times with methylene chloride and the extract was washed with an aqueous sodium chloride solution and dried. The methylene chloride layer was separated into two parts.

Part I

The solvent was evaporated in vacuo. The residue was triturated in ethyl acetate and n-hexane to yield a solid (1.81 g, 81%) of 1'-methoxycarbonyl-2'-oxopropan-1'-yl ester of 7-phenylacetamido-3-methyl-3-cephem-4-carboxylic acid, mp 110°–120° C.

The product was purified by a silica-gel chromatography (benzene : ethyl acetate = 4 : 1 ). mp. 119°–122° C, IR : 1765 cm$^{-1}$, UV $\lambda$max : 259 n.m.
Elemental Analysis for $C_{21}H_{22}N_2O_7S$,
Calculated ; C 56.46 H 4.96 N 6.27.
Found ; C 56.57 H 4.97 N 6.23.

Part II

To the cooled methylene chloride solution were added several drops of an aqueous solution of sodium tungustate or vanadium pentaoxide under cooling and stirring. 40% peracetic acid, 0.76 g was gradually dropped in the mixture. Further peracetic acid will be added to the mixture, when found to be needed by TLC. Aftr completing the reaction, the reaction mixture was diluted with ice-water and adjusted to pH 7.5 with ammonia. The separated aqueous layer was well extracted with methylene chloride. The organic layers were combined, washed with an aqueous sodium chloride, dried and evaporated in vacuo. The residue was treated with isopropanol and n-hexane to yield 1'-methoxycarabonyl-2'-oxopropan-1'-yl ester of 7-phenylacetamido-3-methyl-3-cephem-4-carboxylic acid 1-oxide (mp 144°–147° C) Yield : 1.97 g (85%).

The product was purified by a silica-gel chromatography (ethyl acetate). mp 169°–170° (decomp.), IR : 1775 cm$^{-1}$,UV $\lambda$max : 254 n.m.

EXAMPLE 3

Each of esters of 6-phenylacetamidopenam-3-carboxylic acid was treated in accordance with Example 2.
The products were as follows:

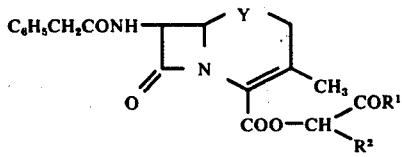

| No. | $-CH\genfrac{}{}{0pt}{}{COR^1}{R^2}$ | Y | Yield (%) | mp (° C) | IR (cm$^{-1}$) |
|---|---|---|---|---|---|
| 3-a | —CH(COCH$_3$)COC$_6$H$_5$ | S | 82 | 123~126* | 1770 |
| 3-b | —CH(COCH$_3$)COOC$_2$H$_5$ | S | 78 | 100~103** | 1765 |
| 3-c | —CH(COC$_6$H$_5$)COOC$_2$H$_5$ | S | 74 | 40~60 (decomp.) | 1765 |
| 3-d | —CH(COCH$_3$)CON(CH$_3$)$_2$ | S | 73 | 206~207 (decomp.) | 1765 |
| 3-e | —CH(COCH$_3$)CON⟨morpholino⟩ | S | 67 | 218~220 | 1765 |
| 3-f | —CH(COCH$_3$)COC$_6$H$_5$ | S-O | 85 | ~179 (decomp.) | 1775 |
| 3-g | —CH(COCH$_3$)COOC$_2$H$_5$ | S-O | 84 | solid | 1775 |
| 3-h | —CH(COC$_6$H$_5$)COOC$_2$H$_5$ | S-O | 84 | 160~183 (decomp.) | 1775 |

\* Anal.: C$_{24}$H$_{24}$N$_2$O$_6$S Calculated; C 63.40, H 4.91 N 5.69 Found; C 63.54 H 4.94 N 5.65
\*\* Anal.: C$_{22}$H$_{24}$N$_2$O$_7$S Calculated; C 57.39 H 5.25 N 6.08 Found; C 57.09 H 5.27 N 5.95

EXAMPLE 4

Each of esters of 6-phenoxyacetamidopenam-3-carboxylic acid 1-oxide was treated in accordance with Example 2. The products were as follows:

| No. | $-CH\genfrac{}{}{0pt}{}{COR^1}{R^2}$ | Y | Yield (%) | mp (° C) | IR (cm$^{-1}$) |
|---|---|---|---|---|---|
| 4-a | —CH(COCH$_3$)$_2$ | S | 78 | syrupy | 1770 |
| 4-b | —CH(COCH$_3$)COC$_6$H$_5$ | S | 77 | solid | ″ |
| 4-c | —CH(COCH$_3$)COOCH$_3$ | S | 81 | ″ | ″ |
| 4-d | —CH(COCH$_3$)COOC$_2$H$_5$ | S | 78 | syrupy | ″ |
| 4-e | —CH(COCH$_3$)CON(CH$_3$)$_2$ | S | 7 | solid | ″ |
| 4-f | —CH(COCH$_3$)CON⟨morpholino⟩ | S | 65 | 179~180 | ″ |

Each 1-oxides of the above compounds were amorphous solid which is difficult to crystallize.

EXAMPLE 5

1'-Methoxycarbonyl-2'-oxopropan-1'-yl ester of 6-phenylacetamido-penam-3-carboxylic acid 1-oxide was treated in each of various catalysts instead of pyridine salt of dichloromethylphosphonic acid in Example 2 in accordance with Example 2.

The results were as follows:

| No. | Catalyst (Used moles to one mol. of the ester) | Yield (%) I | II |
|---|---|---|---|
| 5-a | pyridine 2,2,2-trichloroethyl-phosphate (0.03 ~ 0.05) | 82 | 87 |
| 5-b | picoline trichloromethyl-phosphonate (0.03) | 72 | 78 |
| 5-c | piperidine hydrogen bromide (0.05 ~ 0.1) and pyridine (0.1) | 71 | 85 |
| 5-d | piperidine hydrogen bromide (0.05 ~ 0.1) and acetic acid (0.005) or phosporic acid (0.003) | 76 | 83 |
| 5-e | p-toluenesulfonic acid (0.03) and pyridine (0.05) | 43 | 74 |
| 5-f | salton (0.03) and pyridine (0.05) | 38 | 65 |
| 5-g | pyridine phenylphosphate (0.05) | 53 | 68 |
| 5-h | No catalyst (10 mins at 150 ~ 160° C in dimethylsulfoxide) | 38 | 57 |
| 5-i | POBr$_3$ (0.01) and pyridine (0.08) | 67 | 91 |

I: 1'-methoxycarbonyl-2'-oxopropan-1'-yl ester of 7-phenylacetamido-3-methyl-3-cephem-4-carboxylic acid.
II: 1-oxide of the above I.

REFERENCE EXAMPLE 1

(Preparation of Starting Material)

To a suspension of 11.6 g (30 m.m.)of potassium penicillin V in 12 ml of dimethylformamide and 12 ml of acetone, were added 5.00 g (33 m mol) of methyl α-chloroacetoacetate. The mixture was stirred at about 50° C for 2 days and concentrated in vacuo to remove acetone. The residue was taken up ethyl acetate, washed with a cool 4% sodium hydrogen carbonate solution, water and then an aqueous sodium chloride saturated solution, dried over magnesium sulfate and evaporated to dryness. The green oily residue was 12.8 g (92%).

The resulted 1'-methoxycarbonyl-2'-oxopropan-1'-yl ester of penicillin V (12.8 g, 27.7 m mol) was added in 30 ml of dichloromethane cooled in an ice-bath, and 40% peracetic acid (6.9 ml, 41.6 m mol) was stirred in, drop by drop. After 30 min. the mixture was evaporated in vacuo, and the residue was taken up 50 ml of ethyl acetate, adjusted to pH 7 with a cooled 4% sodium hydrogen carbonate solution. The organic layer was washed with water (two times), and with a saturated sodium chloride solution. The dried organic layer was evaporated to yield an oily residue, after which it was triturated in isopropyl ether to obtain a pale yellow power (10.4 g, 78%) of 1'-methoxycarbonyl-2'-oxopropan-1-yl ester of penicillin V 1-oxide, mp. 64°–66° C.

REFERENCE EXAMPLE 2

(Preparation of Starting Material)

Potassium penicillin G was treated in a similar way to Reference example 1 and the resulting oil was triturated in ethanol-ethyl ether to give a powder; it was recrystallized from ethanol-ethyl ether to obtain 5.2 g (85%) of 1'-methoxycarbonyl:2'-oxopropan-1'-yl ester of penicillin G-1-oxide, mp. 134°–135° C.

REFERENCE EXAMPLE 3

(Hydrolysis of Ester Group)

To a suspension of 4.3 g of 2', 4'-dioxopentan-3'-yl7-phenylacetamido-3-methyl-3-cephem-4-carboxylate in 20 ml of acetone were added 10 ml of an aqueous solution containing 1g of sodium nitrite, while stirring under cooling. In order to comlete the reaction, further 1 g of sodium nitrite and 1 ml of acetic acid were portionwise added to the reaction mixture and warmed at 50°–55° for a short time. After comfirming the completion of reaction by TLC, the mixture which was adjusted to pH 7.5 was distilled in vacuo to remove acetone. The aqueous solution was washed with methylene chloride, adjusted to pH 1.5 and cooled. The precipitated crystals were washed with a little amount of cooled water and dried. The aqueous layer was saturated with sodium chloride and extracted with ethyl acetate. The extract was washed with a little amount of an aqueous sodium chloride solution, dried and distilled in vacuo to remove the solvent. 7-Phenylacetamido-3-methyl-3-cephem-4-carboxylic acid of total yield 3.1 g (95%) was obtained. mp. 180°–184° C(decomp.) Recrystallation from methanol and n-hexane gave mp 191°–192° (decomp.). IR : 1770 $cm^{-1}$. UV $\lambda max$ : 260 n.m.

What I claim is:

1. A compound having the formula:

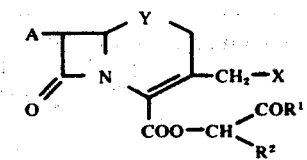

wherein A is phenylacetamido, phenoxyacetamido, formylamino, phthalimido, 2,2-dimethyl-3-nitroso-;b 4-phenyl-5-oxo-imidazolin-1-yl or 2-methyl-3-nitroso-4-phenyl-5-oxo-imidazolin-1-yl; Y is =S or =S—O; X is hydrogen or lower alkanoyloxy; $R^1$ is lower alkoxy, lower alkyl or phenyl and $R^2$ is lower alkoxycarbonyl, lower alkylcarbonyl or phenyl carbonyl, or a group of the formula;

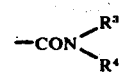

in which $R^3$ and $R^4$, which may be the same or different, are hydrogen or lower alkyl or may, together with the nitrogen atom to which they are bonded and an oxygen atom, together form morpholino.

2. A compound according to claim 1, in which A is phenylacetamido group.

3. A compound according ro claim 1, in which A is phenoxyacetamido group.

4. 1'Methoxycarbonyl-2'-oxopropan-1'-yl ester of 7-phenylacetamido-3-methyl-3-cephem-4-carboxylic acid or its 1-oxide according to claim 1.

5. 1'-Methoxycarbonyl-2'-oxopropan-1'-yl ester of 7-phenoxyacetamido-3-methyl-3-cephem-4-carboxylic acid or its 1-oxide according to claim 1.

6. 1'-Ethoxycarbonyl-2'-oxopropan-1'-yl ester of 7-phenylacetamido-3-methyl-3-cephem-4-carboxylic acid or its 1-oxide according to claim 1.

7. 1'-Ethoxycarbonyl-2'-oxopropan-1'-yl ester of 7-phenoxyacetamido-3-methyl-;b 3-cephem-4-carboxylic acid or its 1-oxide according to claim 1.

8. 2', 4'-Dioxopentan-3'-yl ester of 7-phenylacetamido-3-methyl-3-cephem-4-carboxylic acid or its 1-oxide according to claim 1.

9. 2',4'-Dioxopentan-3'-yl ester of 7-phenoxyacetamido-3-methyl-3-cephem-4-carboxylic acid or its 1-oxide according to claim 1.

* * * * *

UNITED STATES PATENT OFFICE
CERTIFICATE OF CORRECTION

Patent No. 4,022,773          Dated May 10, 1977

Inventor(s) Toshiyasu Ishimaru          Page 1 of 2

It is certified that error appears in the above-identified patent and that said Letters Patent are hereby corrected as shown below:

Column 1, line 21, "lower aralkyl" should read: -- lower alkyl, aralkyl --; Column 1, line 22, "alkoxycarabo-" should read: -- alkoxycarbo- --; Column 2, line 7, "dibensoylmethyl" should read: -- dibenzoylmethyl --; Column 2, line 8, "acetyl-ethoxycaronylmethyl" should read: -- acetyl-ethoxycarbonylmethyl -- ; Column 2, line 9, "di(methoxylcarbonyl)methyl" should read: -- di(methoxycarbonyl)methyl --; Column 2, line 23, "methyl-3-methyl-3-cephem-4-carboxylic" should read: -- methyl-3-cephem-4-carboxylic --; Column 2, line 24, "1'ethoxycarbonyl-2'-oxopropan:1'yl" should read: -- 1'-ethoxycarbonyl-2'-oxopropan-1'-yl --; Column 2, line 29, "thylaminocarabonylmethyl eser" should read: -- thylaminocarbonylmethyl ester --; Column 3, line 9, "phosphonate pyridine" should read: -- phosphonate, pyridine --; Column 3, line 42, "chloroethylophosphoric" should read: -- chloroethylphosphoric --; Column 4, line 2, "2',4'-dioxopenton" should read: -- 2',4'-dioxopentan --; Column 4, line 49, "Aftr" should read: -- After --;

UNITED STATES PATENT OFFICE
CERTIFICATE OF CORRECTION

Patent No. 4,022,773      Dated May 10, 1977

Inventor(s) Toshiyasu Ishimaru      Page 2 of 2

It is certified that error appears in the above-identified patent and that said Letters Patent are hereby corrected as shown below:

Column 7, line 13, "1'-methoxycarbonyl:2'-" should read: -- 1'-methoxycarbonyl-2'- --; Column 7, line 19, "-3'-yl7-" should read: -- -3'-yl 7- --; Column 8, line 10, "2,2-dimethyl-3-nitroso-;b" should read: -- 2,2-dimethyl-3-nitroso- --; Column 8, line 40, "-methyl-;b 3-cephem-4-car-" should read: -- -methyl-3-cephem-4-car- --

Signed and Sealed this sixteenth Day of August 1977

[SEAL]

Attest:

RUTH C. MASON
*Attesting Officer*

C. MARSHALL DANN
*Commissioner of Patents and Trademarks*